United States Patent
Choi et al.

(10) Patent No.: US 7,755,039 B2
(45) Date of Patent: Jul. 13, 2010

(54) 3-DIMENSIONAL DIFFERENTIAL PUMPING SYSTEM AND METHOD THEREOF

(75) Inventors: Myoung Choul Choi, Seoul (KR); Jong Shin Yoo, Daejeon (KR); Hyun Sik Kim, Daejeon (KR)

(73) Assignee: Korea Basic Science Institute, Daejeon (KR)

( * ) Notice: Subject to any disclaimer, the term of this patent is extended or adjusted under 35 U.S.C. 154(b) by 164 days.

(21) Appl. No.: 12/293,258

(22) PCT Filed: Oct. 26, 2007

(86) PCT No.: PCT/KR2007/005304

§ 371 (c)(1), (2), (4) Date: Sep. 16, 2008

(87) PCT Pub. No.: WO2008/054093

PCT Pub. Date: May 8, 2008

(65) Prior Publication Data

US 2009/0039254 A1    Feb. 12, 2009

(30) Foreign Application Priority Data

Oct. 31, 2006    (KR) .................. 10-2006-0106609

(51) Int. Cl.
*H01J 37/301* (2006.01)
*B01D 59/44* (2006.01)

(52) U.S. Cl. .................. 250/289; 250/441.11; 250/288

(58) Field of Classification Search .................. 250/289, 250/288, 441.11
See application file for complete search history.

(56) References Cited

U.S. PATENT DOCUMENTS 6,002,130 A * 12/1999 Kato .......................... 250/289
6,032,513 A *  3/2000 Chorush et al. ............ 73/23.35
6,087,657 A *  7/2000 Kato .......................... 250/288

FOREIGN PATENT DOCUMENTS

JP       53-23267 A    3/1978
JP    2005-248934 A    9/2005

OTHER PUBLICATIONS

PCT International Search Report (PCT/ISA/210) and Written Opinion (PCT/ISA/237), PCT International Patent Application No. PCT/KR2007/005304, Feb. 4, 2008.

* cited by examiner

*Primary Examiner*—Nikita Wells
(74) *Attorney, Agent, or Firm*—Fenwick & West LLP

(57) ABSTRACT

A differential pumping system in which a vacuum chamber is manufactured to have a plurality of vacuum pumps and conductance limit plates between the vacuum pumps. The differential pumping system in which an ion is implanted from an ionization source, passes through the vacuum chamber and is detected by a detection unit includes a plurality of vacuum pumps in the vacuum chamber and one or more conductance limit plates between the vacuum pumps, and the conductance limit plates form an angle less than 90° with the transmission direction of the ion. According to such a constitution, higher degree of vacuum and the ion transmission efficiency are maintained without increasing the length of the vacuum chamber. Furthermore, it is possible to minimize the attenuation of an ion detection signal due to a collision with a neighboring neutral molecule, improving the sensitivity of an ion detection device.

10 Claims, 2 Drawing Sheets

[Fig. 1]
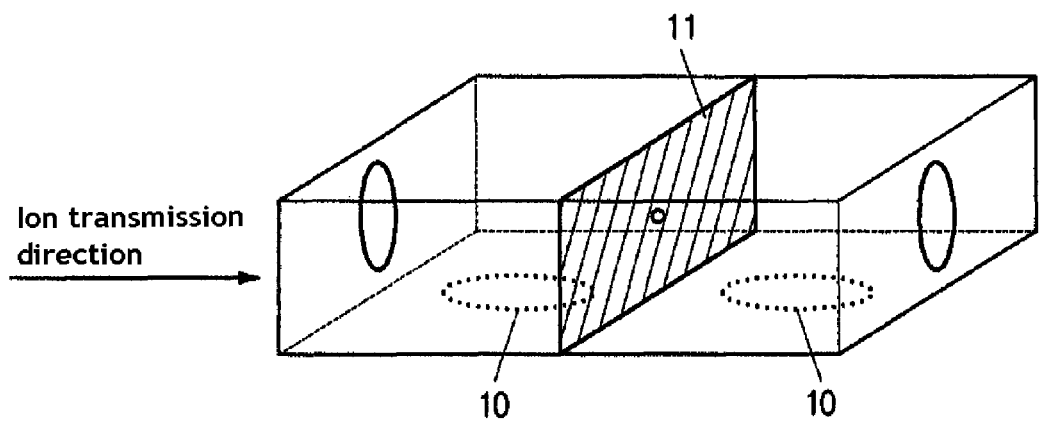
[Fig. 2]
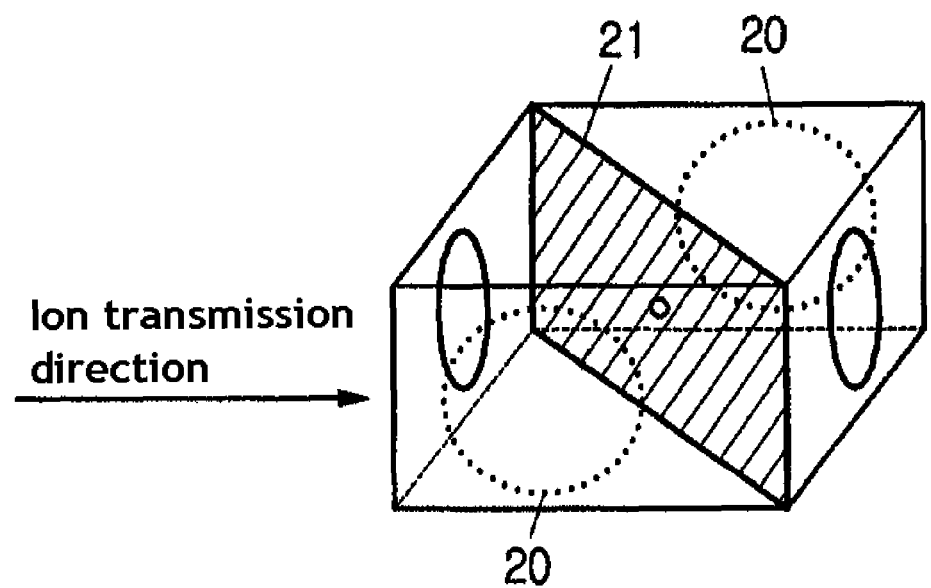

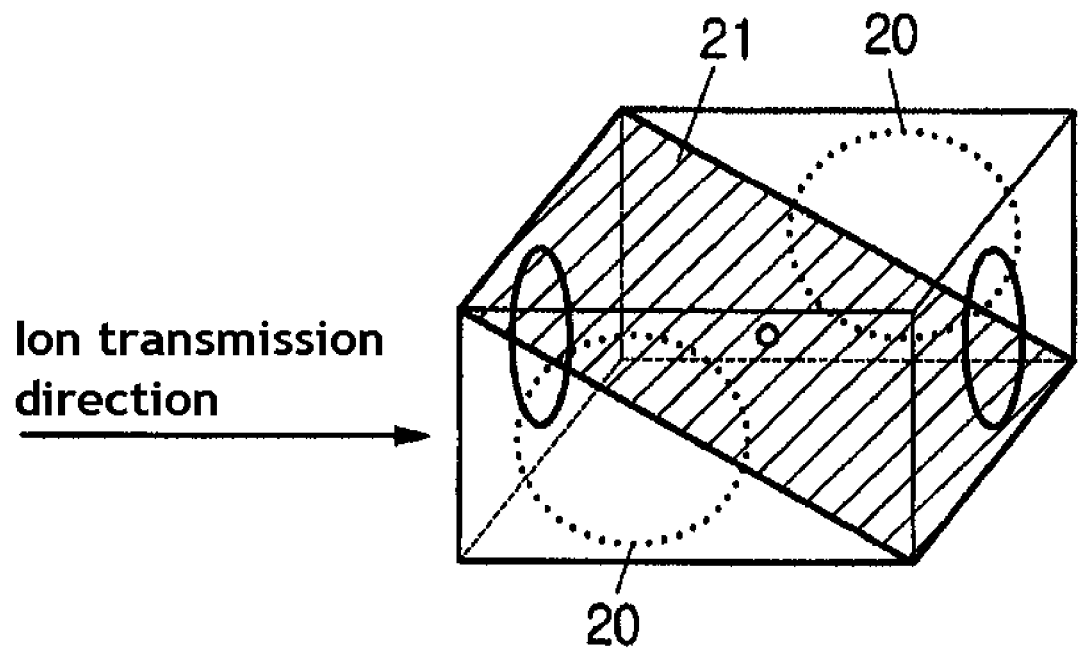
[Fig. 3]
Ion transmission direction

3-DIMENSIONAL DIFFERENTIAL PUMPING SYSTEM AND METHOD THEREOF

TECHNICAL FIELD

The present invention relates to a high efficiency differential pumping system and a method thereof that improve the ion transmission efficiency by minimizing the transmission length while raising the degree of vacuum of a measuring instrument in a mass spectrometer. More particularly, the present invention relates to a differential pumping system and a method thereof that are devised to improve the ion transmission efficiency and the detection sensitivity of an ion detector by manufacturing a vacuum chamber to be equipped with more number of vacuum pumps without increasing the length thereof and thus minimizing the ion transmission length while forming a high vacuum state.

BACKGROUND ART

A mass spectrometer such as a conventional Fourier transform ion cyclotron resonance mass spectrometer (FT-ICR MS) is configured to produce an ion from a to-be-analyzed sample using a device such as an electrospray ionization (ESI) source in the outside and then to implant the ion into a detection unit. Hence, the space between the ionization source and the detection unit should be opened, and the detection unit should be maintained at a very low pressure, i.e., ultra high vacuum pressure, differently from the ionization source under atmospheric pressure.

Accordingly, in order to implant the ion from the ionization source under atmospheric pressure while maintaining the detection unit in an ultra high vacuum state, a differential pumping system in which gas molecule conductance limit plates are installed for every vacuum chamber transmitting the ion is used. However, it is not possible to extend the length of an ion transmission portion because the ion transmission efficiency decreases rapidly as the length of the transmission path becomes longer, and thus it has been difficult to form an ultra high vacuum state in the detection unit.

FIG. 1 is a schematic view illustrating a differential pumping system according to a conventional technology. As illustrated in FIG. 1, according to a conventional differential pumping system, two vacuum pumps 10 are linearly arranged along a line in a vacuum chamber, and a conductance limit plate 11 is installed between the compartments in which the vacuum pumps 10 are arranged.

Here, the conductance limit plate 11 is a plate that has a small orifice at its center and the remaining portions of which are blocked. The conductance limit plate 11 passes only ions concentrated by an electric field and limits the movement of neighboring neutral gas molecules.

According to the differential pumping system as illustrated in FIG. 1, because the vacuum pumps for the differential pumping operation are sequentially arranged on a straight line, the length of the vacuum chamber is greatly extended as the number of the vacuum pumps is increased in order to form an ultra high vacuum state, so that it is not possible to maintain the length of an ion transmission portion.

That is, although it is possible to form a higher vacuum state, the decrease of the ion transmission efficiency cannot be avoided. As such, according to the prior art, because vacuum pumps are sequentially arranged on a straight line along a vacuum chamber, it has not been possible to simultaneously improve the degree of vacuum and the ion transmission efficiency.

DISCLOSURE OF INVENTION

Technical Problem

The present invention is conceived to solve the aforementioned problems in the prior art. An object of the present invention is to provide a differential pumping system and a method thereof that simultaneously ensure the ultra high degree of vacuum and the ion transmission efficiency by enabling a plurality of vacuum pumps and one or more conductance limit plates to be equipped three-dimensionally without extending the length of a vacuum chamber.

Another object of the present invention is to improve the sensitivity of an ion detection device by providing an ultra high vacuum environment and minimizing the attenuation of an ion detection signal due to a collision with a neighboring neutral molecule.

Technical Solution

An exemplary embodiment of the present invention provides a differential pumping system in which an ion is implanted from an ionization source, passes through a vacuum chamber and is detected by a detection unit, the differential pumping system includes a plurality of vacuum pumps which are arranged within the vacuum chamber and one or more conductance limit plates which are arranged between the vacuum pumps within the vacuum chamber, and the conductance limit plates are arranged to form an angle less than 90° with the transmission direction of the ion implanted from the ionization source.

Another exemplary embodiment of the present invention provides a differential pumping method which uses the differential pumping system, the differential pumping method includes a step of implanting an ion into a vacuum chamber, a step of passing the ion implanted into the vacuum chamber through a plurality of vacuum pumps having a difference of the degree of vacuum, and a step of detecting the ion passing through the plurality of vacuum pumps within the vacuum chamber by a detection unit.

ADVANTAGEOUS EFFECTS

By way of the constitution of a differential pumping system according to an embodiment of the present invention in which a vacuum chamber is equipped with a plurality of three-dimensionally arranged vacuum pumps and one or more conductance limit plates installed between the vacuum pumps, it is possible to maintain higher degree of vacuum while maintaining the ion transmission efficiency without extending the length of the vacuum chamber. That is, it is possible to simultaneously improve the ion transmission efficiency and maintain an ultra high vacuum state by minimizing an ion transmission portion.

Furthermore, it is possible to minimize the attenuation of an ion detection signal due to a collision with a neighboring neutral molecule by providing an ultra high vacuum environment, so that it is possible to improve the sensitivity of an ion detection device.

BRIEF DESCRIPTION OF THE DRAWINGS

FIG. 1 is a schematic view illustrating a conventional differential pumping system;

FIG. 2 is a schematic view illustrating a differential pumping system according to an embodiment of the present invention; and FIG. 3 is a schematic view illustrating a differential pumping system according to another embodiment of the present invention.

MODE FOR THE INVENTION

The present invention has attained the result of improving the ion transmission efficiency and the degree of vacuum by manufacturing a differential pumping system having a three-dimensional arrangement configuration different from the conventional linear arrangement configuration, that is, by adding a vacuum system pump without increasing the length of an ion transmission portion.

Specifically, a differential pumping system according to the present invention in which an ion is implanted from an ionization source, passes through a vacuum chamber and is detected by a detection unit includes a plurality of vacuum pumps that are three-dimensionally arranged in the same space of the vacuum chamber and one or more conductance limit plates that are arranged between the vacuum pumps within the vacuum chamber and spatially divide the respective vacuum pumps. The conductance limit plates according to the present invention are arranged obliquely to form an angle less than 90° with the transmission direction of the ion implanted from the ionization source.

Hereinafter, preferred embodiments of the present invention will be described with reference to the accompanying drawings.

FIG. 2 is a schematic view illustrating a differential pumping system according to an embodiment of the present invention, and FIG. 3 is a schematic view illustrating a differential pumping system according to another embodiment of the present invention.

As illustrated in FIGS. 2 and 3, unlike the constitution illustrated in FIG. 1 in which two vacuum pumps 10 are sequentially arranged along a line, a differential pumping system according to an embodiment of the present invention is configured such that a vacuum chamber is provided to have two vacuum pumps 20 three-dimensionally arranged in the same space and a conductance limit plate 21 arranged between the two vacuum pumps 20 in the direction obliquely dividing the vacuum chamber. Hence, the obliquely arranged conductance limit plate 21 forms an angle less than 90° with the transmission direction of the ion implanted from the ionization source.

As such, the differential pumping system according to an embodiment of the present invention is configured to form a difference of the degree of vacuum between two sections of the vacuum chamber by installing the conductance limit plate between the compartments in which the two vacuum pumps are provided.

Comparing FIG. 1 with FIGS. 2 and 3, it can be understood that the conventional differential pumping system of FIG. 1 is improved to the differential pumping system of FIG. 2 or 3 according to the embodiment of the present invention.

That is, according to the differential pumping system of FIG. 2 or 3, the differential pumping system is manufactured not in the conventional linear arrangement configuration as illustrated in FIG. 1, but in a three-dimensional arrangement configuration, so that it is possible to simultaneously improve the ion transmission efficiency and the degree of vacuum because it is possible to maintain the length of an ion transmission portion even when a vacuum pump is further added to form an ultra high vacuum state.

As such, a plurality of vacuum pumps can be used, and the vacuum pumps are arranged three-dimensionally on the top and the bottom or the left and the right in the same space of the vacuum chamber. Here, the conductance limit plates are arranged between the vacuum pumps within the vacuum chamber.

Meanwhile, in a Fourier transform ion cyclotron resonance mass spectrometer (FT-ICR MS) system using a superconducting magnet, if it is difficult to arrange a differential pumping system so that the vacuum pump is adjacent to a high magnetic field, then it is not possible to ensure a high vacuum state at the detection portion inside the magnetic field.

Hence, in case the space is specially limited by the magnetic field and so forth, it becomes possible to construct a differential pumping system that ensures the ion transmission efficiency and allows the formation of an ultra high vacuum state using the abovementioned differential pumping system of the present invention.

According to the abovementioned embodiments of the present invention, by way of the constitution of a differential pumping system in which a vacuum chamber is equipped with a plurality of three-dimensionally vacuum pumps and one or more conductance limit plates are installed between the vacuum pumps, it is possible to simultaneously improve the ion transmission efficiency and maintain an ultra high vacuum state by minimizing an ion transmission portion. Furthermore, it is possible to minimize the attenuation of an ion detection signal due to a collision with a neighboring neutral molecule by providing an ultra high vacuum environment, thereby improving the sensitivity of an ion detection device.

The scope of the present invention is not limited to the embodiments and drawings described and illustrated above. It will be apparent that those skilled in the art can make various modifications and changes thereto within the scope of the present invention.

INDUSTRIAL APPLICABILITY

The present invention relates to a high efficiency differential pumping system and a method thereof that improve the ion transmission efficiency by minimizing the transmission length while raising the degree of vacuum of a measuring instrument in a mass spectrometer. More particularly, the present invention relates to a differential pumping system and a method thereof that are devised to improve the ion transmission efficiency and the detection sensitivity of an ion detector by manufacturing a vacuum chamber to be equipped with more number of vacuum pumps without increasing the length thereof and thus minimizing the ion transmission length while forming a high vacuum state.

The invention claimed is:

1. A differential pumping system in which an ion is implanted from an ionization source, passes through a vacuum chamber and is detected by a detection unit, the differential pumping system comprising:
    a plurality of vacuum pumps which are arranged within the vacuum chamber; and
    one or more conductance limit plates which are arranged between the vacuum pumps within the vacuum chamber, wherein the conductance limit plates are arranged to form an angle less than 90° with the transmission direction of the ion implanted from the ionization source.

2. The differential pumping system as claimed in claim 1, wherein the plurality of vacuum pumps are respectively arranged above and below or left and right of the conductance limit plate interposed therebetween in the vacuum chamber.

3. The differential pumping system as claimed in claim 1, wherein the conductance limit plates have an orifice at center and are blocked up at remaining portions except the center, and the conductance limit plates pass only an ion concentrated by an electric field and limit the movement of a neighboring neutral gas molecule.

4. The differential pumping system as claimed in claim 1, wherein the inner space of the vacuum chamber is divided into a plurality of sections by the conductance limit plates, and the conductance limit plates form a difference of the degree of vacuum between the plurality of sections of the vacuum chamber.

5. The differential pumping system as claimed in claim 1, wherein the plurality of three-dimensionally arranged vacuum pumps and the conductance limit plates are applied to a Fourier transform ion cyclotron resonance mass spectrometer (FT-ICR MS) system.

6. A differential pumping method using the differential pumping system according to claim 1 comprising the steps of:
 implanting an ion into the vacuum chamber;
 passing the ion implanted into the vacuum chamber through a plurality of vacuum pumps having a great difference of the degree of vacuum; and
 detecting the ion passing through the plurality of vacuum pumps within the vacuum chamber by a detection unit.

7. The differential pumping method as claimed in claim 6, wherein the plurality of vacuum pumps are arranged respectively above and below or left and right of the conductance limit plate interposed therebetween in the vacuum chamber.

8. The differential pumping method as claimed in claim 6, wherein the conductance limit plates have an orifice at center and are blocked up at remaining portions except the center, and the conductance limit plates passes only an ion concentrated by an electric field and limit the movement of a neighboring neutral gas molecule.

9. The differential pumping method as claimed in claim 6, wherein the inner space of the vacuum chamber is divided into a plurality of sections by the conductance limit plates, and the conductance limit plates form a difference of the degree of vacuum between the plurality of sections of the vacuum chamber.

10. The differential pumping method as claimed in claim 6, wherein the respective steps are applied to a Fourier transform ion cyclotron resonance mass spectrometer (FT-ICR MS) system.

* * * * *